United States Patent [19]

Kameswaran et al.

[11] 4,046,799

[45] Sept. 6, 1977

[54] α-CYANO BENZYL-2-NAPHTHALENEACETATES

[75] Inventors: Venkataraman Kameswaran, Pennbrook, Pa.; Roger William Addor, Pennington, N.J.

[73] Assignee: American Cyanamid Company, Stamford, Conn.

[21] Appl. No.: 673,244

[22] Filed: Apr. 2, 1976

[51] Int. Cl.$^2$ .................... A01N 9/20; C07C 121/66
[52] U.S. Cl. .................... 260/465 D; 260/465 R; 260/515 R; 260/544 B; 424/304; 424/308; 560/100
[58] Field of Search .................... 260/465 D

[56] References Cited

U.S. PATENT DOCUMENTS 3,835,176   9/1974   Matsuo et al. .................... 260/465 D 3,896,157   7/1975   Fried et al. .................... 260/465 D X Primary Examiner—Dolph H. Torrence
Attorney, Agent, or Firm—H. G. Jackson

[57] ABSTRACT

Insecticidal agents substituted-benzyl α-$C_1$-$C_4$ alkyl-2-naphthaleneacetates, are provided having the formula:

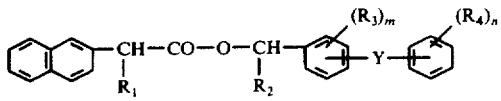

wherein $R_1$ represents alkyl $C_1$-$C_4$; $R_2$ is H, —CN or —C≡$CR_5$; $R_3$ and $R_4$ each represent halogen or methyl; $m$ and $n$ each represent an integer from 0, 1 and 2; Y represents O, S or $CH_2$ and $R_5$ represents H or alkyl $C_1$-$C_4$.

6 Claims, No Drawings

α-CYANO BENZYL-2-NAPHTHALENEACETATES

BACKGROUND OF THE INVENTION

1. Field of the Invention

The invention pertains to new chemical compounds useful as insecticides.

2. Description of the Prior Art

British Pat. No. 969,068 (1964) discloses α-substituted 1-naphthylacetic acids and pharmaceutical compositions containing these acids. Acidi Naftilacetici- by Casadio, Pala, Bruzzese, Marazzi Uberti, Farmaco Edizione Scientifica 17: 797-817 (1962); 1-naphthylacetic and 2-naphthylacetic acid derivatives; studies on the relationship between chemical structure and choleretic activity, Marazzi-Uberti, Turba and Bianchi, Research Laboratories of Istituo DeAngeli, Milan, Italy (1966); condensed aromatic compounds Chemical Abstracts 1549 (1963) and 16026 (1964) and 16027, Vol. 61.

SUMMARY OF THE INVENTION

The invention is compounds of the formula:

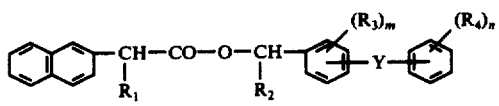

wherein $R_1$ is alkyl $C_1$-$C_4$, $R_2$ is H, CN or —C=$CR_5$, $R_3$ and $R_4$ each represent halogen or methyl, $m$ and $n$ each represent an integer 0, 1 or 2, Y is O, S or $CH_2$, and $R_5$ is H or alkyl $C_1$-$C_4$; their manufacture; and their use for controlling insects and acarids.

DETAILED DESCRIPTION OF THE INVENTION

The invention relates to novel benzyl-α-alkyl-2-naphthaleneacetates represented by the formula:

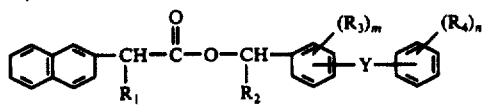

wherein $R_1$ is alkyl $C_1$-$C_4$; $R_2$ is H, —CN or —C=$CR_5$; $R_3$ and $R_4$ each represent halogen or methyl; $m$, and $n$ each individually represent an integer selected from 0, 1 and 2; Y represents oxygen, sulfur or methylene and $R_5$ is hydrogen or alkyl $C_1$-$C_4$. The invention relates to a method for controlling insects and acarina with the above-mentioned compounds by contacting the pests and/or applying to their habitat, breeding ground and/or their food supply, an insecticidally or acaricidally effective amount of the compound having the structure shown above. The invention relates to a method for protecting agronomic crops and homothermic animals from insect and acarid attack, by topically applying to the animals or to the foliage of the crops an effective amount of a compound having the above-identified structure.

The term "halogen" as used in this specification means chlorine, fluorine, bromine and iodine.

Preferred compounds of this invention have the above structure wherein $R_1$ is a $C_2$-$C_3$ alkyl; $R_2$ is —CN or H; Y is oxygen; and, $m$ and $n$ are each 0.

Still more preferred compounds have the formula:

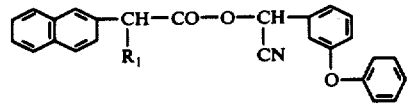

wherein $R_1$ is isopropyl, n-propyl or ethyl; and most preferred is the compound wherein $R_1$ is isopropyl. This latter compound is of special interest and importance by reason of its superior insecticidal activity and its unique miticidal activity.

In accordance with this invention, compounds depicted by the formula I below:

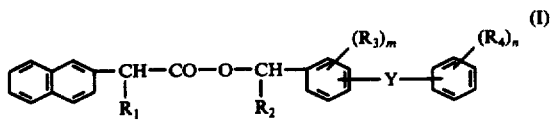

wherein $R_1$, $R_2$, $R_3$, $R_4$, $R_5$, Y, $m$, and $n$, are as described above, can be prepared by reaction of approximately equimolar amounts of a 2-naphthylacetyl halide (II) preferably the chloride, and a benzyl alcohol (III), preferably a m-phenoxybenzyl alcohol. The reaction is generally conducted in the presence of a hydrocarbon or halocarbon solvent such as heptane, toluene, xylene, ethylene chloride or the like, at a temperature between about 0° C and 30° C, and preferably in the presence of an acid acceptor such as pyridine, triethylamine, or aqueous sodium hydroxide.

Using pyridine as representative of the acid acceptor, the reaction may be illustrated as follows:

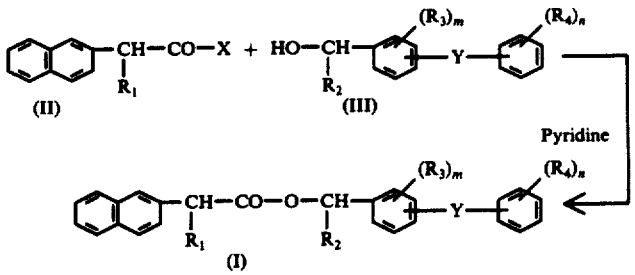

wherein $R_1$ is alkyl $C_1$-$C_4$; $R_2$ is H, —CN or —C=$CR_5$; $R_3$ and $R_4$ are halogen or methyl; $m$ and $n$ are, individually, integers selected from 0, 1 and 2; Y is O, S or $CH_2$, $R_5$ is H or alkyl $C_1$-$C_4$, and X is chlorine or bromine.

The formula (II) naphthaleneacetylhalide can be obtained by reaction of the appropriate alkylated-2-naphthalene-acetic acid with a thionyl halide such as thionyl chloride or thionyl bromide, or a phosphorus halide such as phosphorus trichloride, phosphorus tribromide or phosphorus pentachloride in the presence of an organic solvent such as toluene, methylene chloride, benzene or a benzene hexane mixture. The halide and the acid are employed in approximately equimolar amounts, although as much as two mole equivalents of the halide per mole of acid may be used, and the reaction is preferably conducted at about the refluxing temperature of the solvent, generally between about 40° C and 110° C. This reaction may be graphically illustrated as follows:

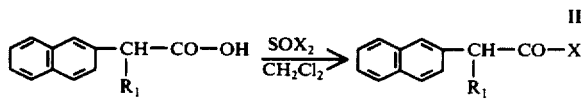

wherein $R_1$ and X are as previously described.

The alkylated-2-naphthaleneacetic acid, employed in the above-illustrated reaction, can be prepared from the commercially available 2-naphthaleneacetonitrile. The process involves reacting approximately equimolar amounts of 2-naphthaleneacetonitrile and an alkyl halide represented by the formula: $R_1X$, wherein $R_1$ is alkyl $C_1$-$C_4$ as defined above and X is halogen, such as chloro, iodo or bromo. An excess of the alkyl halide may, of course, be used. This reaction is conducted in the presence of an anhydrous ammoniacal base and an aprotic solvent such as toluene, xylene, diethylether or the like. The reaction yields the corresponding alkylated-2-naphthaleneacetonitrile which is then readily hydrolyzed to the alkylated-2-naphthaleneacetic acid. This reaction is conducted with a strong mineral acid and water at an elevated temperature, preferably a temperature between 120° C and 150° C. The reactions can be graphically illustrated as follows:

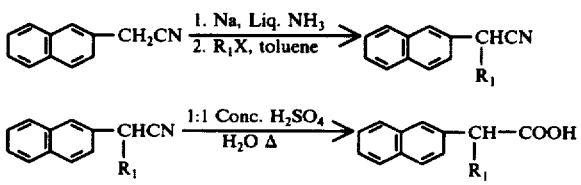

wherein $R_1$ and X are as described above.

The preparation of α-tert-butyl-2-naphthaleneacetonitrile is carried out using 2-naphthaldehyde by the following sequence of reactions (1) reaction with t-butyl magnesium chloride, (2) conversion of the neopentyl alcohol to the choride using thionyl chloride, (3) preparation of the Grignard reagent with magnesium in tetrahydrofuran, and, (4) carboxylation with carbon dioxide.

Typical aprotic solvents which can be employed in the alkylation of 2-naphthaleneacetonitrile include, toluene, xylenes, benzene, methylcyclohexane, dimethoxyethane and the like.

The above alkylation can be conducted using commercially available sodium amide or on alkali amide prepared in situ from sodium or potassium metal in liquid ammonia. Following removal of excess ammonia, the alkylation proceeds in the presence of an aprotic solvent preferably at a temperature between 50° C and 120° C.

An alternate route to the alkylation of 2-naphthaleneacetonitrile and one which is preferred in large-scale reactions is to use $R_1X$ as the alkylating agent in the presence of aqueous alkali, e.g. 50% aqueous sodium hydroxide, as the base. The reaction is promoted by phase-transfer catalysis, such catalysis being of the quaternary ammonium or quaternary phosphonium salt or crown ether types. Suitable quaternary ammonium or phosphonium salts include benzyltriethylammonium chloride, tetrabutylammonium hydrogen sulfate, cetyltrimethylammonium chloride, tricaprylmethylammonium chloride, hexadecyltributylphosphonium bromide, and the like. These salts may be incorporated to the extent of about 0.5 to 100 mole percent based on the moles of starting acetonitrile used. Suitable crown ethers include 18-crown-6, dibenzo-18-crown-6, and dicyclohexyl-18-crown-6. Crown ethers are used in the range of 0.5 to 5 mole percent based on the moles of the nitrile used.

Typical acids which can be employed in the conversion of the alkylated-2-naphthaleneacetonitrile to the corresponding acid, are sulfuric acid, hydrochloric acid, phosphoric acid, and mixtures thereof. For the conversion, the presence of water in the reaction mixture is essential and we have found that the reaction appears to proceed satisfactorily only at elevated temperatures and preferably between 120° and 150° C. Somewhat higher or lower temperatures may be used, but excessive temperatures cause charring of the reaction mixture and at low temperatures the reaction does not proceed at an acceptable rate.

The compounds of this invention are highly effective insecticidal and acaricidal agents. As such, they are useful for destroying harmful insects and acarina which are the vectors for disease which plague both man and animal.

Advantageously, the compounds of this invention are also effective against insects and acarina that attack, damage and/or destroy many agronomic crops including cereals, cole crops, cucurbits, ornamentals, shrubs, citrus and deciduous fruit trees, cotton, legumes and solanaceous plants.

For control of insects and acarids and protection of growing plants and/or harvested crops, including stored grain, the compounds of this invention may be applied to the foliage of plants, the insects and/or acarids habitat and/or their food supply. Generally, the active compound is applied in the form of a dilute liquid spray; however, it may also be applied as an aerosol, a dust, dust concentrate, or the like.

Liquid sprays which are particularly useful are oil sprays, flowable liquids, emulsifiable concentrates and wettable powders which are dispersed and/or diluted with water or other relatively inexpensive liquid diluent for application.

A typical emulsifiable concentrate useful for protecting cotton, cereals, cole crops, cucurbits, ornamentals, shrubs and the like, may comprise about 24% to 27% by weight of the active ingredient; 10% by weight of a "matched pair" emulsifiers, such as toximul D and toximul H, sold by Stepan Chemical Company or a blend of alkylpolyethoxylate and sodium salt of alkylsulfonatedalkylate; and 63% to 66% by weight a solvent such as xylenes.

Advantageously, the compounds of this invention are highly effective as contact and stomach poisons and thus can be used effectively for the control of the pests by application to their habitat and/or for protection of agronomic crops by application thereto.

The invention is further demonstrated by the examples set forth below.

EXAMPLE 1

Preparation of α-Isopropyl-2-naphthaleneacetonitrile

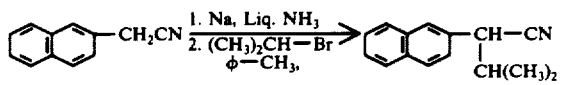

Anhydrous liquid ammonia (700 ml) is introduced through an inlet tube into a 4-necked flask equipped with a cold-finger condenser (dry ice-isopropanol trap) and a mechanical stirrer. A few crystals of hydrated ferric nitrate is added, followed by sodium (34.2 g, 1.485 mole) over a 1 hour period. The reaction mixture is stirred for 30 minutes to dissolve all the sodium. When the blue color changes to gray completely, a solution of 2-naphthaleneacetonitrile (225.7 g, 1.35 mole) in toluene (800 ml) is then added carefully over a 2½ hour period. The cold-finger condenser is replaced by an ordinary condenser (no water flow) and the red-brown reaction mixture is allowed to stir overnight with loss of most of the ammonia. The last traces of ammonia are removed by heating the reaction mixture to 55° C. 2-Bromopropane (189.0 g, 1.54 mole) is then added at 55° C to 60° C over 2 hour period. This treatment requires no external heating. After the addition, the reaction mixture is refluxed for 3 hours and cooled to room temperature. The reaction mixture is admixed with water (800 ml) and the organic phase is separated from the aqueous phase. The aqueous phase is extracted twice with benzene (2 × 150 ml). The combined organic phases are then washed with water, saturated sodium chloride and then evaporated to an oil (312 g). Vacuum distillation gives the product: α-isopropyl-2-naphthaleneacetonitrile, (264.3, 94%); b.p. 137° C (0.2 mm).

This procedure is repeated in all essential details excepting that isobutyl bromide (1-bromo-2-methylpropane) is substituted for 2-bromopropane. This latter procedure yields α-isobutyl-2-naphthaleneacetonitrile. When the procedure is repeated with sec-butylbromide the corresponding α-sec-butyl-2-naphthaleneacetonitrile is obtained.

EXAMPLE 2

Preparation of α-sec-butyl-2-naphthaleneacetonitrile

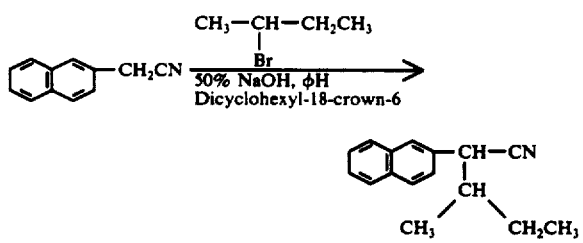

A mixture of 2-naphthaleneacetonitrile (30.00 g, 0.179 mole), dicyclohexyl-18-crown-6 [1.60 g, 0.0043 mole (2.4 mole %)], 2-bromobutane (50.20 g, 0.366 mole), benzene (80 ml) and sodium hydroxide solution (50%, 80 ml) is stirred at room temperature for 16 hours. The organic layer is diluted with ether (250 ml), separated, washed successively with water, dilute hydrochloric acid and water and dried over sodium sulfate. Evaporation and distillation under vacuum gives α-sec-butyl-2-naphthaleneacetonitrile (34.3 g, 86%); b.p. 130° C (0.1 mm).

Analysis calculated for $C_{16}H_{17}N$: C, 86.05; H, 7.68; N, 6.27. Found: C, 85.91; H, 7.76; N, 5.96.

EXAMPLE 3

Preparation of α-isobutyl-2-naphthaleneacetonitrile

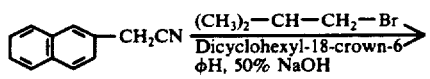

Using isobutyl bromide instead of sec-butyl bromide and 5.8 mole percent of dicycylohexyl-18-crown-6 as in Example 2, repetition of the above experiment gives α-isobutyl-2-naphthaleneacetonitrile in 79% yield; b.p. 120° C to 130° C (0.025 mm.)

EXAMPLE 4

Preparation of α-Isopropyl-2-naphthaleneacetic acid

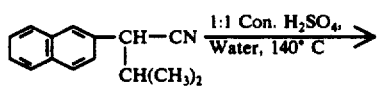

A mixture of α-isopropyl-2-naphthaleneacetonitrile (264.3 g, 1.263 mole), concentrated sulfuric acid (660 ml) and water (660 ml), is heated at 140° C. for 12 hours. The mixture is allowed to cool slowly during which the acid precipitates. The solid is collected by filtration, washed thoroughly with cold water (4 × 500 ml), and dried in a vacuum oven at 50° C. The yield is 281 g (97.6%). The solid is taken up in hexane (750 ml) and benzene (750 ml) and brought to boiling. The cloudy solution on cooling gives a white crystalline solid, which is collected and dried; (227 g, 2 crops, 78.8%); m.p. 129°-130° C. An analytical sample prepared in another run has a m.p. of 130°-131° C.

Analysis: Calculated for $C_{15}H_{16}O_2$ (228.18): C, 78.92; H, 7.06. Found: C, 79.12; H, 7.30.

Following the above-procedures but substituting α-isobutyl-2-naphthaleneacetonitrile, or α-sec-butyl-2-naphthaleneacetonitrile for α-isopropyl-2-naphthaleneacetonitrile yields respectively, α-isobutyl-2-naphthaleneacetic acid; and α-sec-butyl-2-naphthaleneacetic acid.

EXAMPLE 5

Preparation of α-Isopropyl-2-naphthylacetyl chloride

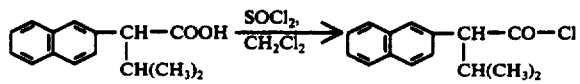

A suspension of α-isopropyl-2-naphthaleneacetic acid (205.5 g, 0.90 mole) in methylene chloride (1500 ml) and thionyl chloride (119.0 g, 1.0 mole) is gently refluxed for 20–22 hours. The clear brown solution is evaporated at 45°-50° C. using a water aspirator to give the crude acid chloride (219 g, 98.6%), which is used as such for esterification.

EXAMPLE 6

Preparation of α-Cyano-m-phenoxybenzyl, α-isopropyl-2-naphthaleneacetate

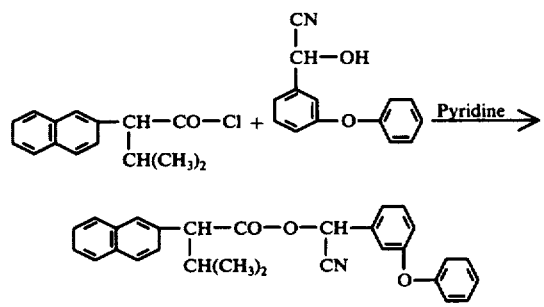

α-isopropyl-2-naphthaleneacetate and the corresponding m-phenxoybenzyl α-isobutyl, α-sec-butyl and α-tert-butyl-2-naphthaleneacetates, are likewise effective insecticidal agents.

The latter compounds are prepared as above-indicated, excepting that m-phenoxybenzyl alcohol is substituted for α-cyano-m-phenoxybenzyl alcohol. Analysis for m-phenoxybenzyl α-isopropyl-2-naphthaleneacetate is as follows: Calculated: C, 81.92; H, 6.39. Found: C, 81.66; H, 6.46.

Additional compounds prepared by the above procedure but substituting the appropriate α-alkyl $C_1C_4$-2-naphthaleneacetylhalide for α-isopropyl-2-naphthaleneacetylchloride and using the appropriate m-phenoxybenzyl alcohol yields the products set forth in Table I below:

Table I

Insecticidal Compounds Having the Structure

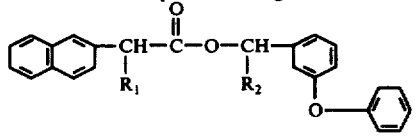

| Name | $R_1$ | $R_2$ | Calculated C | Calculated H | Found C | Found H |
|---|---|---|---|---|---|---|
| m-Phenoxybenzyl α-iso-propyl-2-naphthalene-acetate | —CH(CH$_3$)$_2$ | —H | 81.92 | 6.39 | 81.66 | 6.46 |
| m-Phenoxybenzyl α-ethyl-2-naphthaleneacetal | —C$_2$H$_5$ | " | 81.79 | 6.10 | 80.86 | 6,13 |
| m-Phenoxybenzyl α-(n)-propyl-2-naphthalene-acetate | —C$_3$H$_7$(n) | " | 81.92 | 6.39 | 80.82 | 6.65 |
| α-Cyano-m-phenoxybenzyl α-ethyl-2-naphthalene-acetate* | —C$_2$H$_5$ | —CN | — | — | — | — |
| α-Cyano-m-phenoxybenzyl α-(n)-propyl-2-naphthalene acetate | —C$_2$H$_7$(n) | " | — | — | — | — |
| α-Cyano-m-phenoxybenzyl α-sec-butyl-2-naphthalene-acetate | —CHC$_2$H$_5$<br>\|<br>CH$_3$ | —CN | 80.15 | 6.06 | 79.27 | 6.19 |
| α-Cyano-m-phenoxybenzyl α-i-butyl-2-naphthalene-acetate | —CH—CH(CH$_3$)$_2$ / CH$_3$ | —CN | 80.15 | 6.06 | 80.05 | 6.21 |

\* = Identified by NMR
— = No data

A solution of α-ispropyl-2-naphthaleneacetyl chloride (219 g, 0.887 mole) in benzene (350 ml) is added to a solution of α-cyano-m-phenoxybenzyl alcohol, 179.8 g, 0.798 mole) and pyridine (70.2 g, 0.887 mole) in ether (750 ml) at 0°–10° C. over a 1¼ hour period. Pyridine hydrochloride precipitates out during the addition. The reaction mixture, after stirring overnight at room temperature, is diluted with more ether (500 ml) and poured into water (1200 ml). The organic phase is separated, washed with water, 10% H$_2$SO$_4$ and water and dried over Na$_2$SO$_4$. Evaporation gives an orange-brown gum (348 g, 100% crude yield, 87.5% purity by liquid chromatography). Calculated for C$_{29}$H$_{25}$NO$_3$; C, 79.98, H, 5.79; N, 3.22. Found: C, 79.88; H, 5.89; N, 3.12.

The thus-prepared α-cyano-m-phenoxybenzyl α-isopropyl-2-napththaleneacetate is a highly effective insecticidal agent. Similarly the corresponding α-cyano-m-phenoxybenzyl α-isobutyl, α-sec-butyl and α-tert-butyl-2-naphthaleneacetates, are also useful as insecticidal agents. Additionally, it is noted that m-phenoxybenzyl

EXAMPLE 7

Insecticide Testing Procedures

Test Formulations

A. 1000 PPM of test compound in 65% acetone 35% water mixtures.

B. 300 PPM of test compound in 50% acetone 50% water mixtures.

C. 10 PPM of test compound in acetone.

Initial Tests

Malaria Mosquito — *Anopheles quadrimaculatus* Say — Egg Test

One ml of a 300 ppm solution is pipetted into a 400 ml beaker containing 250 ml of deionized water and stirred with the pipette, giving a concentration of 1.2 ppm. A wax paper ring 0.6 cm wide to fit inside the beaker is floated on the surface of the test solution to keep the eggs from floating up the meniscus curve and drying out on the side of the glass. A spoon made of screen is used to scoop up and transfer about 100 eggs (0–24 hours old) into the test beaker. After 2 days at 80° F., observations of hatching are made. This includes kill of eggs or inhibition of hatch, kill of newly hatched larvae, or delayed hatch. Additional observations are made after another day for the same effects.

Tobacco Budworm — *Heliothis virescens* (Fabricius)

A cotton plant with 2 true leaves expanded is dipped for 3 seconds with agitation in a 300 ppm solution. A 1.25 to 2 cm square of cheesecloth with about 50 to 100 budworm eggs 0–24 hours old is also dipped in the test solution and placed on a leaf of the cotton plant, all being placed in the hood to dry. The leaf with the treated budworm eggs is removed from the plant and placed in an 8 oz Dixie cup with a wet 2 inch piece of dental wick and covered with a lid. The other leaf is placed in a similar cup with a wick and a piece of cheesecloth infested with 50–100 newly hatched larvae is added before covering the cup with a lid. After 3 days at 80° F., observation of egg hatch are made, as well as kill of newly hatched larvae, any inhibition of feeding, or interference of any sort with normal development.

Two-Spotted Spider Mite— *Tetranychus urticae* (Koch)

Sieva lima bean plants, with primary leaves 7.6 to 10 cm long, are infested with about 100 adult mites per leaf 4 hours before use in this test, in order to allow egg-laying before treatment. The infested plants are dipped for 3 seconds with agitation into a 300 ppm solution, and the plants set in the hood to dry. After 2 days at 80° F., the adult mite mortality is estimated on one leaf under a 10× stereoscopic microscope. The other leaf is left on the plant an additional 5 days and then examined at 10× power to estimate the kill of eggs and of newly-hatched nymphs, giving a measure of ovicidal and residual action, respectively.

Southern Armyworm — *Spodoptera eridania* (Cramer)

A Sieva lima bean plant with just the primary leaves expanded to 7.6 to 10 cm is dipped for 3 seconds with agitation in a 1,000 ppm solution and set in the hood to dry. Following this, one leaf is placed in a 10 cm petri dish which has a moist filter paper in the bottom and 10 third-instar armyworm larvae about 1 cm long. The dish is covered and held at 80° F. After 2 days mortality counts and estimates of the amount of feeding are made. Compounds showing partial kill and/or inhibition of feeding are held for an extra day for further observations.

All compounds showing activity as defined above are retested, using the second leaf on the bean plant, after an interval of 7 days from original treatment, as an assay of residual activity.

Mexican Bean Beetle — *Epilachna varivestis* Mulsant

Sieva lima bean plant (2 per pot) with primary leaves 7.6 to 10 cm long, are dipped in a 300 ppm solution and set in the hood to dry. One leaf is removed from a plant and placed in a 10 cm petri dish containing a moist filter paper on the bottom and 10 last-instar larvae (13 days from hatching).

The day after treatment, another leaf is removed from the plant and fed to the larvae after removing the remains of the original leaf. Two days after treatment, the third leaf is fed to the larvae, this usually being the last needed. The fourth leaf is used on the third day after treatment if the larvae have not finished feeding. The test is now set aside and held until adults have emerged, usually in about 9 days after treatment began. After emergence is complete, each dish is examined for dead larvae, pupae or adults; deformed pupae or adults; larval-pupal intermediates or pupal-adult intermediates; or any other interference with normal molting, transformation and emergence of pupae or adults.

Western Potato Leafhopper — *Emposca abrupta* DeLong

A lima bean plant with the primary leaf expanded to 7.6 to 10 cm is dipped into a 100 ppm solution and set in the hood to dry. A 1 inch piece of the tip of 1 leaf is cut off and placed in a 10 cm dish with a moist filter paper in the bottom. (In practice, this is usually cut off the tip of a plant from the Mexican bean beetle test or other tests using a bean leaf dipped in the needed solution). From 3 to 10 second-instar nymphs are tapped from the culture plants into the test dish and rapidly covered. Mortality counts are made after 2 days at 80° F.

Bean aphid — *Aphid fabae* Scopoli

Five cm fiber pots, each containing a nasturtium plant 5 cm high and infested with 100 to 500 aphids 2 days earlier are placed on a 4 rpm turntable and sprayed with a 100 ppm solution for 2 revolutions with a No. 154 DeVilbiss Atomizer at 20 psi air pressure. The spray tip is held about 6 inches from the plants and the spray directed so as to give complete coverage of the aphids and the plants. The sprayed plants are laid on their sides on white enamel trays. Mortality estimates are made after 1 day at 70° F.

Malaria mosquito — *Anopheles quadrimaculatus* Say — Adult test

Ten ppm solutions are poured into wide-mouth 56 g. jars each containing a microscope slide. The slides are removed from the test solution with forceps and laid horizontally to dry on a wide-mouth 112 g bottle. When dry, they are placed in the same 112 g bottle and 10 4- to 5-day old mosquitoes of mixed sexes are added to each bottle. A piece of cotton gauze held on by an elastic band serves as a lid and a wad of cotton soaked in 10% honey solution serves as food. Mortality counts are made after 1 day at 80° F.

Tobacco budworm — *Heliothis virescens* (Fabricius) — Third instar.

Three cotton plants with just expanded cotyledons are dipped in a 1,000 ppm solution, and placed in the hood to dry. When dry, each cotyledon is cut in half and 10 are each placed in a 28 g plastic medicine cup containing a 1.25 cm dental wick saturated with water and one third-instar budworm larvae is added. The cup is capped and held for 3 days at 80° F., after which mortality counts are made.

Cabbage looper — *Trichoplusia ni* (Hubner)

A primary leaf of a cotton plant is dipped in the test solution and agitated for 3 seconds. It is then set in a hood to dry. Following this, the leaf is placed in a 10 cm petri dish containing a moist filter paper in the bottom and 10 third-instar loopers. The dish is covered and held at 80° F. After 2 days, mortality counts and estimates of feeding damage are recorded. Those materials showing partial kill and/or inhibition of feeding are held for another day for further observations.

The rating system employed in these tests is as follows:

| Rating System |
| --- |
| 0 = 0–40% killed or affected. |
| 1 = reduced feeding (trace to light damage). |
| 2 = some deformed insects (40–80%). |
| 3 = mostly deformed insects (85–100%). |
| 4 = not an index number at present. |
| 5 = 41–60% mortality. |
| 6 = 61–70% mortality. |
| 7 = 71–85% mortality. |

-continued

| Rating System |
| --- |
| 8 = 86–95% mortality. |
| 9 = 100% mortality. |

The absence of a number indicates that no test has been run at that particular dosage.

Data obtained are reported in Table II below.

Table IIa

| | Insecticide Evaluations | | | | | | | | |
| --- | --- | --- | --- | --- | --- | --- | --- | --- | --- |
| | Mosquito Larvae PPM | | | Budworm Eggs PPM | | | Larvae PPM | | |
| Structure | 1.2 | .4 | .04 | 300 | 100 | 10 | 300 | 100 | 10 |
| Naphthyl–CH(CH(CH$_3$)$_2$)–CO–O–CH$_2$–C$_6$H$_4$–O–C$_6$H$_5$ ** | 9 | 0 | | 0 | 0 | | 9 | 9 | 0 |
| Naphthyl–CH$_2$–CO–O–CH$_2$–C$_6$H$_4$–O–C$_6$H$_5$ | 0 | | | 0 | | | 0 | | |
| Naphthyl–CH(C$_2$H$_5$)–CO–O–CH$_2$–C$_6$H$_4$–O–C$_6$H$_5$ | 9 | | | 0 | | | 8 | 5 | 0 |
| Naphthyl–CH(C$_3$H$_7$-n)–CO–O–CH$_2$–C$_6$H$_4$–O–C$_6$H$_5$ | 9 | | | 0 | | | 9 | 8 | 0 |
| Naphthyl–CH(CH(CH$_3$)$_2$)–CO–O–CH(C≡N)–C$_6$H$_4$–O–C$_6$H$_5$ | 9 | 9 | 9 | 7 | 0 | 0 | 9 | 9 | 8 |
| Naphthyl–CH(CH$_3$)–CO–O–CH(C≡N)–C$_6$H$_4$–O–C$_6$H$_5$ | 9 | 9 | 0 | 0 | | | 9 | 9 | 0 |
| Naphthyl–CH(C$_2$H$_5$)–CO–O–CH(C≡N)–C$_6$H$_4$–O–C$_6$H$_5$ | 9 | 9 | 9 | 9 | 0 | | 9 | 9 | 5 |
| Naphthyl–CH(C$_2$H$_7$-n)–CO–O–CH(C≡N)–C$_6$H$_4$–O–C$_6$H$_5$ | 9 | 9 | 9 | | | | | | |
| Naphthyl–CH(CH$_3$)–CO–O–CH$_2$–C$_6$H$_4$–O–C$_6$H$_5$ | 0 | | | | | | | | |

**Control Compound; No Alkyl Substituent

Table IIb

| | *Mites PPM | | | | Armyworm PPM | | | | Mexican Bean Beetle PPM | | |
| --- | --- | --- | --- | --- | --- | --- | --- | --- | --- | --- | --- |
| Structure | 1000 | 300 | 100 | 10 | 1000 | 100 | 10 | 7 Days | 300 | 100 | 10 |
| Naphthyl–CH(CH(CH$_3$)$_2$)–CO–O–CH$_2$–C$_6$H$_4$–O–C$_6$H$_5$ ** | — | 0 | | | 9 | 9 | 0 | 9 | 9 | 8 | 0 |
| Naphthyl–CH$_2$–CO–O–CH$_2$–C$_6$H$_4$–O–C$_6$H$_5$ | — | 0 | | | 0 | | | | 0 | | |
| Naphthyl–CH(C$_2$H$_5$)–CO–O–CH$_2$–C$_6$H$_4$–O–C$_6$H$_5$ | — | 0 | | | 9 | 0 | | 9 | 0 | | |
| Naphthyl–CH(C$_3$H$_7$-n)–CO–O–CH$_2$–C$_6$H$_4$–O–C$_6$H$_5$ | — | 0 | | | 9 | 0 | | 9 | 0 | | |
| Naphthyl–CH(CH(CH$_3$)$_2$)–CO–O–CH(C≡N)–C$_6$H$_4$–O–C$_6$H$_5$ | — | 9 | 5 | 0 | 9 | 9 | 0 | | 0 | | |

Table IIb-continued

| Structure | *Mites PPM 1000 | 300 | 100 | 10 | Armyworm PPM 1000 | 100 | 10 | 7 Days | Mexican Bean Beetle PPM 300 | 100 | 10 |
|---|---|---|---|---|---|---|---|---|---|---|---|
| 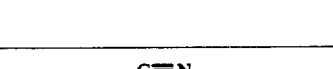 | — | 0 | | | 9 | 0 | | | | | |
| 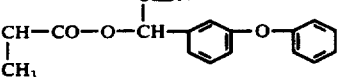 | — | 0 | | | 9 | 9 | 0 | | | | |
|  | — | 0 | | | 9 | 9 | 0 | | | | |
|  | — | 0 | | | O | | | | | | |

*Organophosphorous Resistant
**Control Compound; No Alkyl Substituent

Table IIc

| Structure | Leaf Hopper PPM 100 | 10 | Adult Mosquito PPM 10 | 1 | Aphids PPM 100 | 10 | 1 | TBM PPM 1000 | 100 | Looper PPM 1000 | 100 |
|---|---|---|---|---|---|---|---|---|---|---|---|
| 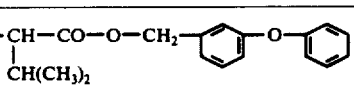 ** | 9 | 0 | 7 | 0 | 9 | 9 | 7 | 9 | 0 | 9 | |
| 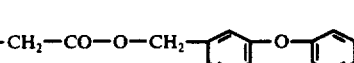 | | | | | | | | | | | |
| 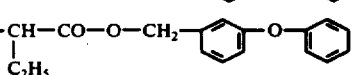 | 9 | 0 | 0 | | 9 | 7 | 0 | 9 | 5 | 0 | |
|  | 0 | 0 | 0 | 0 | 9 | 9 | 9 | 9 | 5 | | |
| 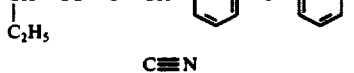 | 9 | 0 | 0 | 0 | 9 | 9 | 9 | 7 | 5 | | |
| 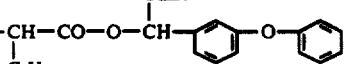 | | | | | | | | | | | |
| 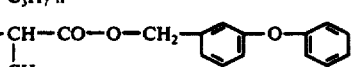 | 9 | 0 | 0 | | 9 | 9 | 0 | 7 | 0 | 0 | |
| 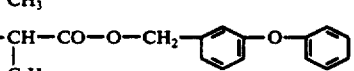 | 9 | 9 | 9 | 6 | 9 | 9 | 9 | 9 | 7 | 9 | 9 |
| 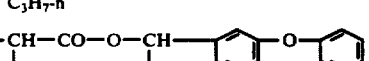 | 0 | 0 | 0 | 0 | 9 | 9 | 0 | 0 | 0 | | |

**Control Compound; No Alkyl Substituent

EXAMPLE 8

Control of Colorado Potato Beetle and Potato Aphids on Potatoes

The following field test is conducted to determine the efficacy of the test compound for the control of Colorado potato beetle, *Leptinotarsa decemlineata* (Say) larvae and potato aphid, *Macrosiphum cuphorbiae* (Thomas) on potato plants.

Application of three spray treatments is made at 2 weeks intervals in May and June using a tractor mounted $CO_2$ powered sprayer with one 120 gallons of dilute emulsion containing 0.11, 0.22 and 0.44 kg active ingredient per hectare. There are threee replications for each treatment located at random in the plot design.

Results are obtained by counting the number of Colorado potato beetle larvae on five plants at random in the center of each treated row per plot. Potato beetle larvae counts are made at 3 to 5 day intervals during May, June and July. Potato aphid counts are made by counting the number of aphids on five plants at random in the center of each treated row of each plot. Aphid counts are made at 5 to 10 day intervals during June and July.

The average number of Colorado potato beetle larvae per five plants is recorded in Table III. The average number of potato aphids per five plants is recorded in Table IV.

In the middle of July, the potato plants in each plot are visually rated according to the amount of foliar damage caused by the feeding of the Colorado potato beetle larvae. The amount of foliar damage is directly proportional to the degree of control of the larvae by the different treatments. The ratings are made according to the following scale:

1 = no foliage remaining
2 = poor foliage
3 = fair foliage
4 = good foliage
5 = excellent foliage The average rating per treatment is recorded in Table III.

Table IV-continued

| | | Average Number Potato Aphids per 5 Plants | | | | | |
| | | Treatment No. I | | | Treatment No. II | | |
| Compound | Rate kg/ha | Sample No. | | | Sample No. | | Foliar Damage Rating |
| | | 1 | 2 | 3 | 4 | 5 | |
| 2-naphthalene acetate | 0.2 | 1.0 | 7.7 | 61.3 | 6.7 | 1 | 3.8 |
| | 0.4 | 0.0 | 4.7 | 50.0 | 10.3 | 0 | 4.5 |
| Check- | | 13.7 | 42.7 | 98.7 | 7.0 | 0 | 1.0 |

EXAMPLE 9

Residual Insecticide Test with Southern Armyworm

Residual Test Procedure

Procedure: Young Sieva lima bean plants (2 per cup) with the first two true leaves well expanded and the apical growing point removed are dipped, with agitation, in a 65% acetone-35% deionized water solution of the compounds. The leaves are permitted to dry and the 0 day leaf samples removed for bioassay before the plants were placed in the greenhouse and maintained under good growing conditions for the remainder of the sampling periods.

Assay of the residual insecticidal persistance is accomplished by removing the appropriate leaves and placing each in a 9 cm petri dish containing a moist 9 cm Whatman No. 1 filter paper and 10 third instar southern armyworm larvae, *Prodenia eridania* (Cramer), the lids replaced and all held in the holding room with constant light at 80° F and 50% relative humidity. Mortality counts and visual estimation of the % feeding damage recorded are made after 72 hours. There were 4 replications of each treatment. The percent feeding damage was obtained by visual estimation.

Data obtained an reported in Table V below.

Table III

| | | Average Number Colorado Potato Beetle Larvae per 5 Plants | | | | | | | | |
| | | Treatment No. I | | | Treatment No. II | | | Treatment No. III | | Foliar Damage Rating |
| Compound | Rate kg/ha | Sample No. | | | Sample No. | | | Sample No. | | |
| | | 1 | 2 | 3 | 4 | 5 | 6 | 7 | 8 | |
| α-Cyano-m-phenoxybenzyl- α-isopropyl-2-naphthaleneacetate | 0.11 | 0.0 | 63.0 | 59.7 | 20.0 | 44.6 | 63.0 | 61.0 | 10 | 1.7 |
| | 0.22 | 0.3 | 9.7 | 5.3 | 3.3 | 3.3 | 54.0 | 6.7 | 7 | 3.8 |
| | 0.44 | 0.0 | 2.3 | 4.3 | 1.0 | 4.7 | 47.7 | 7.3 | 11 | 4.5 |
| Check - | | 40.7 | 136.7 | 120.0 | 155.0 | 178.7 | 166.7 | 57.0 | 8 | 1.0 |

Table IV

| | | Average Number Potato Aphids per 5 Plants | | | | | |
| | | Treatment No. I | | | Treatment No. II | | |
| Compound | Rate kg/ha | Sample No. | | | Sample No. | | Foliar Damage Rating |
| | | 1 | 2 | 3 | 4 | 5 | |
| α-Cyano-m-phenoxybenzyl- α-isopropyl- | 0.1 | 4.3 | 45.7 | 75.7 | 7.6 | 0 | 1.7 |

Table Va

| | | Residual Insecticidal Evaluation Average % Mortality of Southern Armyworm and Average % Feeding on Days Shown | | | | | |
| | | Days Residual 0 | | Days Residual 3 | | Days Residual 6 | |
| Compound | Rate ppm | Average % Kill | Average % Feeding | Average % Kill | Average % Feeding | Average % Kill | Average % Feeding |
| α-Cyano-m-phenoxyphenyl- α-isopropyl-2-naphthalene- acetate | 300 | 100 | 0 | 100 | 0.1 | 100 | 0.03 |
| | 100 | 100 | 0 | 100 | 0.1 | 100 | 0.1 |
| | 30 | 100 | 0 | 80 | 1.9 | 37.5 | 7.8 |
| | 10 | 14.4 | 38.8 | 5 | 8.0 | — | — |
| Check- | — | 0 | 100 | 0 | 93.0 | 0 | 99.0 |
| | | Days Residual 10 | | Days Residual 13 | | Days Residual 17 | |
| Compound | Rate ppm | Average % Kill | Average % Feeding | Average % Kill | Average % Feeding | Average % Kill | Average % Feeding |
| α-Cyano-m-phenoxybenzyl, α-isopropyl-2-naphthalene- acetate | 300 | 100 | 0.1 | 100 | 0.1 | 100 | 0 |
| | 100 | 100 | 0.1 | 90 | 0.1 | 92.5 | 0.1 |
| | 30 | 40 | 28.0 | 2.5 | 31.0 | — | — |
| | 10 | — | — | — | — | — | — |
| Check | — | 0 | 98 | 0 | 98.0 | 0 | 98.0 |

EXAMPLE 10

Control of Lepidopterous Larvae on Collards

The following field test is conducted to determine the efficacy of test compound for the control of cabbage looper, Trichoplusia ni (Huber), imported cabbage worm, Pieris rapae (Linnaeus) and cross-stripped cabbage worm, Evergestis rimosalis (Guenee) on collards.

Application of the dilute emulsion is made with a hand operated back-pack sprayer with a 3 nozzle boom delivering the equivalent of 378 liters of dilute spray per acre containing the equivalent of 0.055, 0.11 and 0.22 kg of actual test compound per hectare. Plots are single rows 7.5 meters long replication 3 times.

Spray applications are made on June 3, 10 and 17. Larval counts on 5 plants at random per plot were made on June 6, 9, 16 and 23. A heavy rain occurred just prior to the counts made on June 9.

The results are given in Table VI as the average number of larvae per five plants per plot.

Table VIa

| | Control of Lepidoptorous Larvae on Collards | | | | |
|---|---|---|---|---|---|
| | | Treatment Date - 6/3 | | | |
| | Rate | Count Date - 6/6 | | Count Date - 6/9 | |
| Compound | kg/ha | Cabbage Looper | Cabbage Looper | Imported Cabbage Worm | |
| α-Cyano-m-phenoxybenzyl, | 0.055 | 9.7 | 5.7 | 1.0 | |
| α-isopropyl-2-naphthalene | 0.11 | 6.0 | 3.7 | 2.3 | |
| acetate | 0.22 | 7.0 | 3.0 | 0.3 | |
| Control | — | 16.3 | 14.7 | 8.3 | |
| | | Treatment Date - 6/10 | | Treatment Date - 6/17 | |
| | Rate | Count Date - 6/16 | | Count Date 6/23 | |
| Compound | kg/ha | Cabbage Looper | *C/S Cabbage Worm | Cabbage Looper | C/S Cabbage Worm |
| α-Cyano-phenoxybenzyl, | 0.055 | 20.0 | 31.7 | 3.7 | 5.3 |
| α-isopropyl-2-naphtha- | 0.11 | 17.7 | 9.7 | 2.0 | 13.3 |
| leneacetate | 0.22 | 12.3 | 18.7 | 2.0 | 3.0 |
| Control | — | 24.3 | 32.7 | 6.0 | 2.0 |

*Cross Striped Cabbageworm

EXAMPLE 11

Control of Apple Aphids on Apples

A field test with α-cyano-m-phenoxybenxyl, α-isopropyl-2-naphthaleneacetate for the control of apple aphids, Aphis pomi DeGeer on apple trees. Thorough coverage of the apple trees is obtained by applying 1140 liters per acre of dilute emulsion at 0.11, 0.22 and 0.44 kg actual compound per hectare with a power sprayer. The spray is directed with a hand operated spray gun. Each plot is a single tree replicated three times at random.

Spray applications are made on May 23, June 9, 25 and July 9. The aphid counts are then made on May 27, June 5, 10, 16, 23, 26, July 2, 8, 10 and 16.

Results are obtained by counting all the aphids on single spurs on each of five branches to random per tree in the three replications. The following table records the average number of aphids per five branches per tree.

Data obtained are reported in Table VII below.

Table VIIa

| Average Number of Aphids on Spurs of 5 Branches per Tree | | | | | | |
|---|---|---|---|---|---|---|
| | | Treatment Date - 5/23 Sample Date | | Treatment Date - 6/9 Sample Date | | |
| | Rate | 5/27 | 6/5 | 6/10 | 6/16 | 6/23 |
| Compound | kg/ha | Aphid Count | | | | |
| α-Cyano-m-phenoxybenzyl, | 0.11 | 29 | 255 | 34 | 25 | 179 |
| α-isopropyl-2-naphtha- | 0.22 | 3 | 236 | 17 | 17 | 25 |
| leneacetate | 0.44 | 7 | 138 | 15 | 10 | 36 |
| Check | — | 122 | 481 | 181 | 107 | 186 |
| | | Treatment Date-6/25 Sample Date | | Treatment Date-7/9 Sample Date | | |
| | Rate | 6/26 | 7/2 | 7/8 | 7/10 | 7/16 |
| Compound | kg/ha | Aphid Count | | | | |
| α-Cyano-m-phenoxybenzyl, | 0.11 | 38 | 40 | 68 | 12 | 5 |
| α-isopropyl-2-naphtha- | 0.22 | 3 | 25 | 108 | 8 | 1 |
| leneacetate | 0.44 | 3 | 30 | 78 | 5 | 0.7 |
| Check | — | 263 | 286 | 394 | 232 | 41 |

EXAMPLE 12

Control of Alfalfa Weevil Larvae and Meadow Spittlebug on Alfalfa

A field test with α-cyano-m-phenoxybenzyl, α-isopropyl-2-naphthaleneacetate is conducted to determine the efficacy of this compound for the control of alfalfa weevil, Hypera postica (Gyllenhal) larvae and meadow spittlebug, Philaenus spumarius (Linneaus) on alfalfa plants.

Application of the spray treatments is made on May 21, with a tractor mounted $CO_2$ powered sprayer with a 7 nozzle boom covering a 4.2 m swath delivering 71 liters of dilute emulsion containing 0.11, 0.22 and 0.44 kg of active ingredient per hectare. There are four replication of each treatment on plots 4.2 m wide by 12 m long located at random in the plot design.

Results are obtained by counting the number of alfalfa weevil larvae obtained by taking 5 random 180° sweeps at with a standard beating net in the first third of each plot on May 22; in the second third of each plot on May 24 and the remainder of the plot on May 28. The meadow spittlebug masses are counted on the same dates by counting the number of spittle masses on 25 alfalfa stems at random per plot. There is a direct correlation between the presence of live spittlebugs and spittle masses. The spittle masses disappear rapidly in the absence of these insects.

The average number of alfalfa weevil larvae per five sweeps per plot and the average number of meadow spittlebug masses per 25 alfalfa stems per plot are recorded in Table VIII below.

Table VIII

| Compound | Rate kg/ha | Average Number Alfalfa Weevil Larvae per 5 Sweeps | | | Average Number Meadow Spittlebug Masses per 25 Stems | | |
|---|---|---|---|---|---|---|---|
| | | Treatment Date - 5/21 Sample Dates | | | | | |
| | | 5/22 | 5/24 | 5/28 | 5/22 | 5/24 | 5/20 |
| α-Cyano-m-phenoxybenzyl, α-isopropyl-2-naphtha-leneacetate | 0.11 | 51.0 | 43.8 | 50.0 | 3.5 | 12.3 | 16.8 |
| | 0.22 | 43.0 | 42.0 | 22.5 | 3.0 | 16.3 | 12.5 |
| | 0.44 | 20.3 | 24.3 | 19.5 | 2.8 | 15.3 | 7.5 |
| Check | — | 126.3 | 149.0 | 90.5 | 5.8 | 20.5 | 21.8 |

Table IX-continued

| Compound | Ixodicidal Activity | |
|---|---|---|
| | Rate ppm | % Mortality |
| | 3.1 | 100 |
| α-Cyano-m-phenoxybenzyl-α-ethyl-2-naphthaleneacetate | 50 | 100 |
| | 12.5 | 100 |
| | 3.1 | 100 |

EXAMPLE 13

Ixodicidal Activity

Effective control of acarina larvae is demonstrated in the following tests with larvae of *Boophilus microplus*, a one-host tick which can remain on a single host through its three life stages, i.e., larvae, nymph and adult. In these tests, a 10% acetone — 90% water mixture contains 3.1, 12.5 or 50 ppm of test compound. Twenty larvae are enclosed in a pipet sealed at one end with a gauze material and solution containing the test compound is then drawn through the pipet with a vacuum hose, the whole simulating a spray system. The ticks are then held for 48 hours at room temperature and mortality is determined. The results achieved are set forth below.

Table IX

| Compound | Ixodicidal Activity | |
|---|---|---|
| | Rate ppm | % Mortality |
| (Control) | | |
| m-Phenoxybenzyl-2-naphthaleneacetate | 50 | 50 |
| m-Phenoxybenzyl-α-ethyl-2-naphthylacetate | 50 | 100 |
| | 12.5 | 100 |
| S-m-Phenoxybenzyl-α-isopropylthio-2-naphthaleneacetate | 50 | 100 |
| | 12.5 | 100 |
| m-Phenoxybenzyl-α-isopropyl-2-naphthaleneacetate | 50 | 100 |
| | 12.5 | 100 |
| α-Cyano-m-phenoxybenzyl-α-isopropyl-2-naphthaleneacetate | 50 | 100 |
| | 12.5 | 100 |

We claim:

1. A compound having the structure:

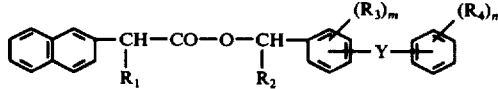

wherein $R_1$ represents alkyl $C_1$–$C_4$; $R_2$ is CN; $R_3$ and $R_4$ each represent halogen or methyl; $m$ and $n$ each represent an integer 0, 1 or 2; and Y represents O, S or $CH_2$.

2. A compound according to claim 1 having the structure:

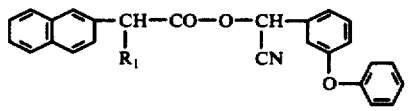

3. A compound according to claim 2 wherein $R_1$ represents a $C_2$–$C_3$ alkyl.

4. A compound according to claim 3 wherein $R_1$ is isopropyl: α-cyano-m-phenoxybenzyl α-isopropyl-2-naphthaleneacetate.

5. A compound according to claim 3 wherein $R_1$ is ethyl: α-cyano-m-phenoxybenzyl α-ethyl-2-naphthaleneacetate.

6. A compound according to claim 3 wherein $R_1$ is n-propyl: α-cyano-m-phenoxybenzyl α-(n)-propyl-2-naphthaleneacetate.

* * * * *